United States Patent
Lesins et al.

[11] Patent Number: 6,156,945
[45] Date of Patent: Dec. 5, 2000

[54] METHOD OF MAKING HIGH PURITY 2,4- AND 3,4-DICHLOROTOLUENE

[75] Inventors: Viesturs Lesins, Tonawanda; Arthur H. Morth, Grand Island; Frank P. Bermel, Orchard Park; David Y. Tang, East Amherst; Mark E. Lindrose, Buffalo; William L. Rueter, Niagara Falls; Dean R. Lagerwall, Amherst; Pravin M. Khandare, Amherst; Hang-Chang Bobby Chen, Amherst; Mark F. Lechner, Sanborn, all of N.Y.

[73] Assignee: Occidental Chemical Corporation, Dallas, Tex.

[21] Appl. No.: 09/428,688

[22] Filed: Oct. 28, 1999

Related U.S. Application Data

[63] Continuation-in-part of application No. 09/193,755, Nov. 17, 1998.
[51] Int. Cl.[7] .................................................. C07C 22/00
[52] U.S. Cl. .......................... 570/209; 570/206; 570/210; 570/211
[58] Field of Search .................... 570/206, 210, 570/211, 209

[56] References Cited

U.S. PATENT DOCUMENTS 4,031,145   6/1977   Di Bella .
4,827,058   5/1989   Mais et al. .

*Primary Examiner*—Alan Siegel
*Attorney, Agent, or Firm*—Richard D. Fuerle; Anne E. Brookes

[57] ABSTRACT

Disclosed is a method of making high purity 2,4- and 3,4-dichlorotoluene from parachlorotoluene that contains some metachlorotoluene. About 0.0001 to about 5 wt % of a Friedel-Crafts catalyst and about 0.5 to about 10 equivalents of a brominating agent are added to the parachlorotoluene. The metachlorotoluene is brominated, but most of the parachlorotoluene is not brominated. Without separating the brominated products from the unbrominated products, about 0.5 to about 1.5 equivalents of a chlorinating agent are added, whereby only the unbrominated products (i.e., the parachlorotoluene) are chlorinated. The resulting 2,4-dichlorotoluene and 3,4-dichlorotoluene can be separated by distillation.

20 Claims, No Drawings

METHOD OF MAKING HIGH PURITY 2,4- AND 3,4-DICHLOROTOLUENE

This application is a continuation-in-part of application Ser. No. 09/193,755, filed Nov. 17, 1998 by V. Lesins et al., titled, "Reducing Meta Content of Isomeric Mixtures of Halo Substituted Toluenes". This application is also related to application Ser. No. 09/429,156 filed of even date by H-C B. Chen et al., titled, "A Method of Increasing Certain Isomeric Ratios in Chlorinating Substituted Benzenes."

BACKGROUND OF THE INVENTION

This invention relates to a method of making 2,4-dichlorotoluene (24DCT) and 3,4-dichlorotoluene (34DCT). In particular, it relates to a method in which parachlorotoluene (PCT) that contains some metachlorotoluene (MCT) is brominated then chlorinated without separating the brominated products from the unbrominated products.

Commercial PCT is made by chlorinating toluene. After distilling off the unreacted toluene and the orthochlorotoluene (OCT), the product is primarily PCT, but small amounts of MCT and OCT are also present, typically about 0.5 to about 1 wt % MCT and about 0.5 to about 1 wt % of the OCT. While OCT can be removed by distillation and the presence of small amounts of the OCT is usually innocuous anyway, it has been found that the presence of MCT can deleteriously affect the properties of the chemicals made from PCT, such as pharmaceuticals, paint pigments, and herbicides. Unfortunately, the boiling point of MCT is close to the boiling point of PCT and the two isomers cannot be easily separated. U.S. application Ser. No. 09/193,755, of which this application is a continuation-in-part, discloses a method of separating PCT from MCT.

If PCT is further chlorinated and no MCT or OCT is present, 24DCT and 34DCT will be the only DCT formed. (If OCT and PCT are present, 4 additional DCTS having similar boiling points can be formed.) Since 24DCT boils at 201° C. and 34DCT toluene boils at 209° C., they can be separated by distillation, giving high purity 24DCT and 34DCT. At present, chlorinating high purity PCT, that is, PCT that contains little or no MCT or OCT, is the only way to obtain 24DCT and 34DCT in high purity.

SUMMARY OF THE INVENTION

We have discovered that high purity 24DCT and 34DCT can be made from PCT that contains some MCT by bromination followed by chlorination in the same pot, that is, without separating the unbrominated products from the brominated products. In the process of this invention, almost all the MCT is brominated and most of the PCT is left unbrominated. When the unbrominated PCT is chlorinated, 24DCT and 34DCT are the only possible DCTS that can be formed. The 24DCT and 34DCT can then be separated by distillation. As an added advantage, any unreacted PCT is of very high purity and is also a valuable product.

The same catalyst can be used for both the bromination reaction and the chlorination reaction. We have further found that the ratio of 24DCT to 34DCT in the product can be raised or lowered by using certain catalysts and cocatalysts.

DESCRIPTION OF THE PREFERRED EMBODIMENTS

The starting material for the process of this invention is PCT that contains about 0.01 to about 10 wt % MCT. Preferably, the PCT contains about 0.1 to about 1 wt % MCT as that is the usual amount of MCT in PCT made by chlorinating toluene (after distilling off OCT and unreacted toluene). The OCT content of the PCT should be less than 0.5 wt % and preferably less than 0.1 wt % as OCT will make some 2,5-dichlorotoluene when it chlorinates.

About 0.0001 to about 5 wt % of a Friedel-Crafts catalyst (also called a "Lewis acid catalyst") is added to the PCT. Preferably, about 0.001 to about 1 wt % catalyst is used as less is less effective and more is usually unnecessary. Examples of suitable Friedel-Crafts catalysts include the chlorides of manganese, molybdenum, titanium, iron, aluminum, zinc, tin, and antimony, and mixtures thereof such as ferric chloride, antimony trichloride, thallium trichloride, zirconium tetrachloride, titanium tetrachloride, sulfuryl chloride, chlorine monooxide, or a mixture thereof. The preferred catalyst is ferric chloride or iron as they are inexpensive, work well, and are used to chlorinate toluene.

The use of about 0.001 to about 5 wt % of a cocatalyst will reduce the ratio of 24DCT to 34DCT (and, conversely, increase the ratio of 34DCT to 24DCT). Preferably, about 0.01 to about 1 wt % of the cocatalyst is used if more 34DCT is desired. Examples of cocatalysts that can be used include sulfur and sulfur compounds such as diphenylsulfide, disulfur dichloride (also called "sulfur monochloride"), thianthrene, thianthrene derivatives, phenoxathiin, phenoxathiin derivatives, phenothiazine, phenothiazine derivatives, iodine, and iodine compounds. The preferred cocatalysts are thianthrene and chlorinated thianthrene, as they are used in the chlorination of toluene, and disulfur dichloride for its effectiveness.

To obtain a high ratio of 24DCT to 34DCT in the product, only a catalyst and no cocatalyst is used for the chlorination reaction.

Examples of suitable brominating agents include liquid or gaseous bromine, BrCl, and sulfuryl bromide ($S_2Br_2$). The preferred brominating agents are liquid bromine and BrCl as they are inexpensive and effective. About ½ to about 10 equivalents of brominating agent should be used per equivalent of MCT. It is preferable to use about 2 to about 5 equivalents of the brominating agent per equivalent of MCT as less may leave some MCT unbrominated and more will result in the loss of PCT to bromination. Generally, proportionally less brominating agent is required at higher concentrations of MCT.

If the starting material was prepared by chlorinating toluene, OCT and unreacted toluene are preferably removed first to prevent their bromination. (Though not preferred, bromination can be performed before distilling off the OCT.) The brominating agent, catalyst, and optional cocatalyst are added to the PCT. The brominating agent can be added before or after the mixture is heated and, though not preferred, the optional cocatalyst can be added after bromination. The reaction temperature can be between about 0° C. and reflux. The preferred temperature range is between room temperature and about 50° C. as at lower temperatures the reaction is slow, although the selectivity is better, while the reverse is true at higher temperatures.

If the brominating agent is bromine, HBr will be formed and will remain in solution. The addition of a chlorinating agent to the solution converts the HBr into additional brominating agent, BrCl. Thus, to prevent the evolution and loss of expensive bromine, one can use about ½ of the desired amount of brominating agent (i.e., about ¼ to about 5 equivalents or, preferably, about 1 to about 2½ equivalents), wait until it reacts, then add a chlorinating agent in an amount about equivalent to the amount of brominating agent added. Examples of suitable chlorinating agents include chlorine gas and sodium chlorate; the preferred chlorinating agent is chlorine as it is inexpensive, readily available, and forms hydrogen chloride as a byproduct, which is easy to remove.

The bromination reaction is more rapid at higher temperatures and higher catalyst concentrations (requiring only about 15 minutes to complete), and can be followed by gas chromatography (GC) to determine its completion. The product mixture will contain unreacted chlorotoluene (CT), typically greater than 95 wt % PCT, and brominated MCT.

Without separating the unreacted CT from the brominated products in the product mixture, the product mixture is chlorinated, which results in the chlorination of the unbrominated products (i.e., the PCT). The chlorination is performed using the same catalyst and optional cocatalyst used for the bromination, and a chlorinating agent, as described hereinabove. A temperature range of about 0° C. to reflux can be used for chlorination, but a temperature of ambient to about 90° C. is preferred as the reaction is slower at lower temperatures and at higher temperatures some trichlorinated product may form. The amount of chlorinating agent used should be about 0.5 to about 1.5 equivalents (based on CT) as less leaves too much unreacted PCT and more can produce trichlorinated products; the preferred amount is about 0.6 to about 0.9 equivalents. While no solvent is needed in these reactions, a solvent can be used if desired.

The product mixture is distilled to separate the products. Unreacted CT, which is a high purity PCT, distills off first. This is followed by 24DCT, then 34DCT, leaving behind the brominated toluenes.

The following examples further illustrate this invention.

EXAMPLE 1

Comparative

PCT was made by chlorinating toluene, then distilling to reduce its OCT content and remove unreacted toluene. One hundred parts by weight (pbw) of the PCT was placed in a reactor fitted with a stirrer, feed inlet, and gas outlet. Ferric chloride catalyst (0.2 pbw) was added, the temperature was raised to 70° C., and gaseous chlorine was introduced to the reaction mixture. As chlorine was consumed, more was added as necessary to maintain the reaction. The progress of the reaction was measured by GC. All of the MCT and about 75 wt % of the PCT were consumed at steady rates over the course of five hours of reaction. The following table gives the composition of the PCT and the product mixture:

|  | Initial PCT (GC area %) | Product (GC area %) |
| --- | --- | --- |
| MCT | 0.53 | 0.0 |
| OCT | 0.04 | 0.0 |
| PCT | 99.43 | 25.5 |
| 24DCT | 0.00 | 45.6 |
| 34DCT | 0.00 | 14.2 |
| 23DCT | 0.00 | 0.1 |
| 25DCT | 0.00 | 0.6 |
| Trichlorotoluene | 0.00 | 11.0 |

This example shows that the undesirable and not easily separated isomers 23DCT and 25DCT are formed when PCT that contains MCT is chlorinated.

EXAMPLE 2

Bromination, Then Chlorination of CT

Using the same PCT and apparatus used in Example 1, 0.3 pbw ferric chloride catalyst and 3.1 pbw liquid bromine were added.

The reaction mixture was mixed at 25° C. for 60 minutes, then the temperature was raised to 70° C. and gaseous chlorine was introduced. As the chlorine was consumed, more was added as necessary to maintain the reaction, which was followed by GC. All of the MCT was consumed during the first two hours of the reaction; the PCT reacted steadily during the five hour period of chlorine addition. The following table gives the composition of the product mixture at the end of six hours of reaction:

|  | Initial PCT (GC area %) | Product (GC area %) |
| --- | --- | --- |
| MCT | 0.53 | 0.0 |
| OCT | 0.04 | 0.0 |
| PCT | 99.43 | 42.7 |
| 24DCT | 0.00 | 35.5 |
| 34DCT | 0.00 | 11.4 |
| Bromochlorotoluene | 0.00 | 3.3 |
| Trichlorotoluene | 0.00 | 8.1 |
| 23DCT | 0.00 | 0.0 |
| 25DCT | 0.00 | 0.0 |

This example shows that 23DCT and 25DCT are not formed from PCT that contains MCT when the PCT is first brominated, then chlorinated. It also shows that a 24DCT/34DCT ratio of 3.1 was obtained when no cocatalyst was used.

EXAMPLE 3

Bromination, Then Chlorination of CT

Example 2 was repeated, except that 0.3 pbw of disulfur dichloride cocatalyst was used with the ferric chloride catalyst and the temperature was raised to 60° C. after 90 minutes. All of the MCT was consumed during the first 90 minutes of reaction. The PCT reacted steadily during the 2.5 hour period of chlorine addition. The following table gives the composition of the starting PCT and the final product mixture:

|  | Initial PCT (GC area %) | Product (GC area %) |
| --- | --- | --- |
| MCT | 0.53 | 0.0 |
| OCT | 0.04 | 0.0 |
| PCT | 99.43 | 58.8 |
| 24DCT | 0.00 | 20.1 |
| 34DCT | 0.00 | 14.3 |
| Bromochlorotoluene | 0.00 | 2.1 |
| Trichlorotoluene | 0.00 | 4.7 |

Like Example 2, this example also shows the benefit of brominating before chlorinating. In this example, the 24DCT/34DCT ratio was 1.4 as a cocatalyst was used.

EXAMPLE 4

Bromination, Then Chlorination of CT

Example 2 was repeated using 322 g PCT, 389 ppm (parts per million, by weight) ferric chloride, and 9.1 g liquid bromine. The cocatalyst was 2 equiv. of chlorinated thianthrene per equiv. of ferric chloride. Bromination was at 41° C. for 2 hrs and chlorination was at 62–63° C. After 95 g of chlorine gas had been added, the chlorine depth was 0.51 and the 24DCT/34DCT ratio was 1.73. After a total of 120 g chlorine gas had been added, the chlorine depth was 0.67 and the 24DCT/34DCT ratio was 1.8.

We claim:

1. A method of making 2,4-dichlorotoluene and 3,4-dichlorotoluene from a mixture of parachlorotoluene containing about 0.01 to about 10 wt % metachlorotoluene comprising
   (A) adding to said mixture
      (1) about 0.0001 to about 5 wt % of a Friedel-Crafts catalyst;
      (2) an optional cocatalyst; and
      (3) about ½ to about 10 equivalents of a brominating agent per equivalent of said metachlorotoluene, whereby said metachlorotoluene is preferentially brominated;
   (B) without separating brominated products from unbrominated products, adding about 0.5 to about 1.5 equivalents of a chlorinating agent, whereby unbrominated parachlorotoluene is chlorinated to form said 2,4-dichlorotoluene and said 3,4-dichlorotoluene; and
   (C) separating said 2,4-dichlorotoluene and 3,4-dichlorotoluene from said mixture by distillation.

2. A method according to claim 1 wherein said brominating agent is BrCl.

3. A method according to claim 1 wherein said brominating agent is liquid bromine.

4. A method according to claim 3 wherein, in step (A), about ½ of the desired amount of said liquid bromine is added followed by about the same equivalents of chlorine gas after said liquid bromine has reacted.

5. A method according to claim 1 wherein said chlorinating agent is chlorine gas.

6. A method according to claim 1 wherein about 0.1 to about 1 wt % of said mixture is metachlorotoluene.

7. A method according to claim 1 wherein said catalyst is ferric chloride or iron.

8. A method according to claim 7 wherein no cocatalyst is present.

9. A method according to claim 7 wherein about 0.001 to about 5 wt % of a cocatalyst is present.

10. A method according to claim 9 wherein said cocatalyst is disulfur dichloride.

11. A method according to claim 9 wherein said cocatalyst is chlorinated thianthrene.

12. A method according to claim 1 wherein said mixture is at about 0° C. to reflux during step (A).

13. A method according to claim 12 where said mixture is at about room temperature to about 50° C. during step (A).

14. A method according to claim 1 wherein said mixture is at about 0° C. to reflux during step (B).

15. A method according to claim 14 wherein said mixture is at about 50 to about 90° C. during step (B).

16. A method according to claim 1 wherein said mixture of parachlorotoluene containing about 0.01 to about 10 wt % metachlorotoluene is obtained by chlorinating toluene and distilling off orthochlorotoluene and unreacted toluene.

17. A method of making 2,4-dichlorotoluene from a mixture that comprises about 90 to about 99.99 wt % parachlorotoluene and about 0.01 to about 10 wt % metachlorotoluene comprising (A) adding to said mixture about 0.1 to about 1 wt % of a catalyst selected from the group consisting of ferric chloride, iron, and mixtures thereof;
   (B) heating said mixture to a temperature between room temperature and about 50° C.;
   (C) adding about 1 to about 2½ equivalents of liquid bromine to said mixture per equivalent of said metachlorotoluene, where no cocatalyst is present in said mixture, whereby metachlorotoluene is brominated but parachlorotoluene is mostly unbrominated;
   (D) after said liquid bromine has reacted, adding to said mixture about the same equivalents, based on the equivalents of said liquid bromine added, of chlorine gas; and
   (E) without separating brominated metachlorotoluene from unbrominated parachlorotoluene, adding about 1.0 to about 1.1 equivalents of chlorine gas to said mixture, whereby said unbrominated parachlorotoluene is chlorinated to form 2,4-dichlorotoluene and 3,4-dichlorotoluene; and
   (F) distilling said mixture to separate said 2,4-dichlorotoluene therefrom.

18. A method according to claim 17 wherein said mixture is at about 50 to about 90° C. during the addition of said chlorine gas.

19. A method of making 3,4-dichlorotoluene from a mixture that comprises about 90 to about 99.9 wt % parachlorotoluene and about 0.01 to about 10 wt % metachlorotoluene comprising (A) adding to said mixture about 0.1 to about 1 wt % of a catalyst selected from the group consisting of ferric chloride, iron, and mixtures thereof and about 0.01 to about 1.0 wt % of a cocatalyst selected from the group consisting of thianthrene, chlorinated thianthrene, disulfur dichloride, and mixtures thereof;
   (B) heating said mixture to a temperature between room temperature and 50° C.;
   (C) adding about 1 to about 2½ equivalents of liquid bromine to said mixture per equivalent of said metachlorotoluene, whereby metachlorotoluene is brominated but parachlorotoluene is mostly unbrominated;
   (D) after said liquid bromine has reacted, adding chlorine gas to said mixture in about the same number of equivalents as equivalents of said liquid bromine added; and
   (E) without separating brominated metachlorotoluene from unbrominated parachlorotoluene, adding about 1.0 to about 1.1 equivalents of chlorine gas to said mixture, whereby said unbrominated parachlorotoluene is chlorinated to form 2,4-dichlorotoluene and 3,4-dichlorotoluene; and
   (F) distilling said mixture to separate said 3,4-dichlorotoluene therefrom.

20. A method according to claim 19 wherein said mixture is at about 50 to about 90° C. during the addition of said chlorine gas.

* * * * *